US012758460B2

(12) United States Patent
Schaaper et al.

(10) Patent No.: US 12,758,460 B2
(45) Date of Patent: Oct. 13, 2026

(54) FEEDBACK SYSTEM AND METHOD FOR PROVIDING FEEDBACK TO WALKING AID USERS

(71) Applicant: BOBErgo B.V., Delft (NL)

(72) Inventors: Martijn Schaaper, Monster (NL); Casper Spoelstra, 's-Gravenhage (NL); Tim Van Den Ing, Rijpwetering (NL)

(73) Assignee: BOBErgo B. V., Delft (NL)

( * ) Notice: Subject to any disclaimer, the term of this patent is extended or adjusted under 35 U.S.C. 154(b) by 52 days.

(21) Appl. No.: 18/901,105

(22) Filed: Sep. 30, 2024

(65) Prior Publication Data

US 2025/0017810 A1 Jan. 16, 2025

Related U.S. Application Data

(63) Continuation of application No. 17/554,360, filed as application No. PCT/NL2020/050396 on Jun. 19, 2020, now Pat. No. 12,127,997.

(30) Foreign Application Priority Data

Jun. 19, 2019 (NL) ..................................... 2023345

(51) Int. Cl.
*A61H 3/04* (2006.01)
*A61B 5/11* (2006.01)
*G01S 7/41* (2006.01)

(52) U.S. Cl.
CPC .............. *A61H 3/04* (2013.01); *A61B 5/1116* (2013.01); *A61H 2201/5023* (2013.01);
(Continued)

(58) Field of Classification Search
CPC ... A61H 3/00; A61H 3/02; A61H 3/04; A61B 5/1116; A61B 5/1118; A61B 5/112;
(Continued)

(56) References Cited

U.S. PATENT DOCUMENTS

2015/0066242 A1 3/2015 Tanaka
2015/0359699 A1 12/2015 Chang et al.
(Continued)

FOREIGN PATENT DOCUMENTS

WO 2006014533 A2 2/2006
WO 2011079320 A1 6/2011
(Continued)

OTHER PUBLICATIONS

International Search Report and Written Opinion—PCT/NL2020/050396—mailing date Sep. 23, 2020.

*Primary Examiner* — Van T Trieu
(74) *Attorney, Agent, or Firm* — Banner & Witcoff, Ltd.

(57) ABSTRACT

System for providing feedback to a user of a walking aid to regulate gait, stance and/or activity irregularities, the system being configured to be installed on a walking aid comprising a frame, at least two wheels, two handles and wherein the frame comprises an intermediate supporting frame between the left and right handles of the frame, the system comprising a configuration of sensors for measuring at least one gait, stance and/or activity indicator, a user profile comprising user gait, stance and activity characteristics, a configuration of at least one stimuli generating devices configured to provide feedback to the user with at least one of a tactile, visual or auditory cue based on the measurements of the sensors and on the user profile.

7 Claims, 7 Drawing Sheets

(52) U.S. Cl.
CPC ................ *A61H 2201/5048* (2013.01); *A61H 2201/5058* (2013.01); *A61H 2201/5064* (2013.01); *G01S 7/415* (2013.01)

(58) Field of Classification Search
CPC ........ G01S 7/415; G01S 13/00; G01S 13/003; G01S 13/56; G01S 13/878; G01S 15/02; G01S 17/08; G05D 1/00; G05D 1/0088; A61G 5/04
See application file for complete search history.

(56) References Cited

U.S. PATENT DOCUMENTS

| | | | |
|---|---|---|---|
| 2018/0178065 A1 | 6/2018 | Yu et al. | |
| 2020/0078258 A1 | 3/2020 | Kanaya et al. | |
| 2022/0211568 A1 | 7/2022 | AlGhazi et al. | |
| 2022/0299619 A1* | 9/2022 | Hu | G01S 7/415 |
| 2024/0280988 A1* | 8/2024 | Dean | G05D 1/0255 |

FOREIGN PATENT DOCUMENTS

| | | |
|---|---|---|
| WO | 2011130223 A1 | 10/2011 |
| WO | 2015063765 A1 | 5/2015 |
| WO | 2016081994 A1 | 6/2016 |

* cited by examiner

Sensor types

| Indicators of stance , gait and/or activity irregularities | A. Camera | B. Force | C. Time | D. Speed | E. Position | F. Movement | G. Inertial | H. Optical | I. Ultrasonic | J. Infrared | K. Radiographic |
|---|---|---|---|---|---|---|---|---|---|---|---|
| 401. Step frequency | ■ | ■ | | ■ | | ■ | | | ■ | ■ | ■ |
| 402. Step size | ■ | ■ | ■ | ■ | ■ | ■ | | | ■ | ■ | ■ |
| 403. Step width | ■ | | | | | ■ | | ■ | ■ | ■ | ■ |
| 404. Ground clearance | ■ | | | | | | | ■ | ■ | ■ | |
| 405. Walking speed | ■ | | ■ | ■ | ■ | | ■ | | | | |
| 406. Walking distance | | | | ■ | ■ | | ■ | | | | |
| 407. User's position relative to the walking aid | ■ | | | | | ■ | | ■ | ■ | ■ | ■ |
| 408. Position of the feet | ■ | | | | | ■ | | ■ | ■ | ■ | ■ |
| 409. Amount of pressure on the walking aid | | ■ | | | | | ■ | | ■ | ■ | |
| 410. The ground contact forces of the feet | | ■ | | | | | ■ | | ■ | ■ | |
| 411. Toe-to-heel walking | ■ | ■ | | | | ■ | ■ | ■ | | | |

■ = a sensor type that might be used to detect the indicator

FIG 4

FEEDBACK SYSTEM AND METHOD FOR PROVIDING FEEDBACK TO WALKING AID USERS

CROSS-REFERENCE TO RELATED APPLICATIONS

This application is a continuation of U.S. patent application Ser. No. 17/554,360, filed Dec. 17, 2021, now allowed, which is a U.S. National Stage application under 35 U.S.C. § 371 of International Application PCT/NL2020/050396 (published as WO 2020/256550 A1), filed Jun. 19, 2020, which claims the benefit of priority to Application NL 2023345, filed Jun. 19, 2019. Benefit of the filing date of these prior applications is hereby claimed. Each of these prior applications is hereby incorporated by reference in its entirety.

FIELD OF THE INVENTION

The present disclosure relates to a system, a walking aid, a method of retrofitting a walking aid and a method for providing feedback cues to a user for regulation and optimization of gait, stance and activity irregularities using a walking aid.

BACKGROUND

Worldwide populations are getting older, resulting in more elderly. In total 20% of the population is expected to have past the age of 60 in 2050, compared to 10% nowadays. Aging is correlated with cognitive, locomotive and sensory impairments that become more severe when people age. These impairments may have a negative effect on the mobility of elderly. 24% of the elderly (aged over 65 years) have mobility problems. Since decreasing mobility is correlated with aging as well, it will get harder and harder for aging people to have an active lifestyle without adaptations and/or assistance.

A decline in mobility can have numerous reasons that can have physical, mental and/or environmental causes. These causes affect each other; environmental causes can for example lead to physical or mental problems. The mobility decline can have a gradual character, which can give a person time to adapt to the situation, but can also get more extreme, e.g. when a person falls and fractures one or more bones. The large variation in causes and decline extremity results in complexity in the creation of an evidence based system that prevents or treats mobility impairment.

Research shows that mobility is an important factor in aging healthy and a restriction in mobility can have severe consequences. Mobility problems can result in social restrictions and limits accessibility to public buildings and shops. It can even lead to social isolation and be a predictor of mortality. Decreased mobility can furthermore lead to osteoporosis, respiratory problems and cardiovascular deconditioning. To prevent these negative consequences of passivity the mobility of elderly needs to be maintained or trained. Even people who have been diagnosed with diseases such as Parkinsonism, Multiple Sclerosis or a Cerebral Infarction, can positively influence their health by exercising.

Parkinsonism is such a disease that can affect one's motor abilities. Parkinsonism is referring to a variety in neurological disorders including Parkinson's disease, vascular Parkinsonism, progressive supranuclear palsy, multiple systems atrophy and other disorders. Symptoms can include a stride reduction, imbalance and a decrease in ground clearance and step size. Ones with Parkinsonism or related disorders could be prone to a 'Freeze of Gait' (FOG) in a later stadium of their disease development. During such a FOG ones are standing still while not being able to initiate a step. It feels like a magnet is pulling their feet down. While experiencing gait irregularities or a FOG, (recurring) triggers have proved to help people in regaining and regulating their gait. Systems that include triggers can help in giving ones with Parkinsonism or related diseases confidence to go out and therefore improves the mobility and independency of an individual.

Multiple Sclerosis (MS) is a neurodegenerative disease for which the majority of patients will experience gait dysfunctions throughout the course of their disease. MS disrupts the nervous system through damaging the myelin sheath of neurons. The damaged nerves show impaired conduction of signals causing physical and mental problems. This may result in lower extremity weakness, spasticity, loss of coordination, imbalance and fatigue. Research evidence shows that medical rehabilitation can limit the severity of the symptoms and can benefit the gait and mobility of the patients. Further research highlights that patients may benefit from education about improving gait safety and efficiency, from a system that continuously reassesses the clinical status of the patient and establishes realistic goals based on this assessment, and from rhythmic auditory stimulation therapy.

A stroke can be another cause of a decrease in mobility. A stroke can result in neurological deficits or impairments. A reduced gait, as a result of hemiplegia, is one of the most common poststroke impairments. Hemiplegic gait is dependent on the residual functions and can therefore widely differ for each patient. Symptoms include muscle weakness, loss of coordination, and paralysis. Gait training can optimize walking performance by increasing muscle strength, coordination and overall fitness. Within gait training programs emphasis is put on balance, ground clearance of the foot, foot placement, step width, step size and cadence. Gait training that focuses on these specific gait parameters proved to have a significant positive effect on the mobility and gait of stroke patients.

No system in the prior art is capable of detecting gait, stance and/or activity irregularities in a robust and/or reliable manner. Furthermore, the prior art uses a very limited number of sensors to measure the walking pattern of a user. No robust, reliable and/or simple system exists in the prior art to monitor the walking pattern of a user. The detection of gait irregularities based on this single sensor (type) does not give insight in the stance and gait characteristics of the users. It only detects pattern differences or the absence of movement. Since the amount of data is limited these systems do only react after a gait irregularity took place.

There is thus a need for improvement in the art.

SUMMARY

Accordingly, a primary object of the present invention is to provide a system for providing feedback to a user of a walking aid to continuously regulate his gait, stance and/or activity irregularities, the system being configured to be installed on a walking aid comprising a frame, at least two wheels, two handles and wherein the frame comprises an intermediate supporting frame between the left and right handles of the frame, the system comprising:

- a configuration of sensors for measuring at least one gait, stance and/or activity indicator comprising at least one of the step frequency, step size, step width, ground clearance, walking speed, amount of pressure on the walking aid, the ground contact forces of the feet, and/or toe-to-heel walking, a user profile comprising user gait, stance and/or activity characteristics, a configuration of at least one stimuli generating device configured to provide feedback to the user with at least one of a tactile, visual or auditory cue based on the measurements of the sensors and on the user profile.

The system allows to stimulate the user to improve his gait and/or stance and/or activity through the use of at least one cue. As soon as the user departs from a target gait or stance, as defined in the user profile, a cue is activated that triggers the user to adapt his gait or stance. Based on the gait and/or stance analysis the user receives feedback and is guided towards a proper posture, position, stance, activity and/or gait. As such an adaptive system can be provided that gives the user feedback. This can be helpful for patients with one of the above mentioned diseases, but may also be very useful for patients in rehabilitation, e.g. recovering from surgery or an accident etc. The latter patients who sometimes need to learn walking again, are very much helped by the regular and irregular stimuli provided by the walking aid. The user profile may thus contain information specific for the disease of the user, or, for rehabilitation patients, it may contain information relating to the stage of their rehabilitation.

Furthermore, placing the sensors on the walking aid has the advantage that the user does not need to place the sensors on his body such as around the foot, leg or waist and the user does not need to carry the device that includes the sensors around. Users of a walker will already have their walker to carry the device and do not have to be equipped an additional device.

Preferably, the configuration of sensors comprises at least one of:

a proximity sensor such as an infrared sensor, an ultrasonic sensor, a time-of-flight sensor or a LIDAR, the proximity sensor being configured to measure the step frequency and/or the step size, and preferably the step width and/or ground clearance, a speed sensor for measuring the walking speed, a force sensor for detecting the amount of pressure provided by the user on the walking aid, the configuration of sensors may further comprise at least one of a camera, a time sensor, a position sensor, a movement sensor, an inertial sensor, an optical sensor, a radiographic sensor.

Using different types of sensor for measuring gait, stance and/or activity irregularities has the advantage that multi-sensor data fusion with the acquired sensor data can be performed. This provides a more accurate gait and stance pattern detection. Furthermore, using different types of sensors also provides the advantage that different types of sensors can be used for measuring the same indicator, and thereby can be used to validate a measurement.

Advantageously, the configuration of at least one stimuli generating device comprises at least one of:

at least one light source for generating a visual cue, an electroacoustic transducer for generating an auditory cue, a vibration unit for generating a tactile cue.

Providing different types of feedback cues has the advantage that the types of cues generated for the user can be adapted to the user, can be alternated, or can even be combined if necessary to provide a stronger cue.

Furthermore, some cues might not be appropriate in specific contexts. A visual cue might not be clearly visible when projected on an uneven ground surface such as high grass, while a loud auditory cue might be annoying for other people when the system starts beeping in a quiet room. Also, some users may prefer a certain type of cue. Switching between cues would allow the system and/or the user to always choose the most, socially or contextually, appropriate cue.

Advantageously, the visual cue comprises the projection of a first line on the ground plane perpendicular to the direction of motion. It has been observed that such a moving forward line provides guidance to the user. Furthermore, users can step over it when experiencing a FOG.

Advantageously, a second and a third light source are configured to generate a visual projection of a second and third line, the second and third line forming a second and third angle with respect to the first line, the second and third angles being preferably in the range of [0, ±45] degrees for each line. When this oblique line is projected, the patient can more easily make a turn. A number of tests performed show that for a number of patients the projection of oblique lines has a favorable effect when the patient is to initiate and/or to follow a turn. Projections of the one or more lines may be provided by a light source, such as a laser light source.

Preferably, the orientation of the projected lines is controlled by a shift such that the user can adapt the orientation of the projected light when making a turn. For example, the user may activate a turn, e.g. by pressing a button on a handle, or by shifting weight onto a handle, or by turning a handle, etc. After activating the turn, the light source may turn, or the second or third light source may project a line under an angle in the direction of the turn, helping the user to initiate the turn and to follow the turn. This helps the user to step towards or over the line, and thus to make the turn. Also upon termination of the turn, the line can be projected straight, i.e. not oblique, again, such that the user can follow a straight line. The termination of the turn may be initiated by the user, or may be predefined, e.g. in order to avoid that the user forgets to initiate the termination of the turn and keeps walking in a circle.

Advantageously, the light source is a laser. A laser source ensures that the required contrast is achieved when the system is to be used in daylight.

Advantageously, the vibration unit is provided in one or two handles of the walking aid.

The advantage of incorporating this module in the handles is that the user also receives a signal in noisy places. In addition, the speed/movement of the walker can be linked to the system. As a result, the vibration can be configured to be only active when the walking aid is moving. This is important for the patient because Parkinson's patients for example have difficulty with dual tasks and different signals preferably are to be avoided in order to be able to perform cognitive tasks again.

Preferably, the electroacoustic transducer comprises at least one of a speaker, a headphone, or an earphone.

Advantageously, the electroacoustic transducer can be configured to produce a periodic or rhythmic sound, wherein preferably the period or rhythm is related to the step frequency. Adapting the rhythm to the user can be beneficial to stimulate the user to walk at a certain pace.

Advantageously, the period or rhythm and/or the tone height can be configured by the user. The user can then set his preferences.

Advantageously, the stimuli generating device can be configured to change the intensity of the cue based on the correction provided by the user to the stance, gait and/or activity irregularity.

The intensity, rate and type of the feedback cue can be adapted by the system based on stored predefined user preference data and/or based on sensors that detect contextual and/or personal parameters. Alterations in the type of cue and in the intensity may minimize habituation effects, make the invention work in all or most types of social and environmental contexts, and apply to the needs of the individual user.

It has been observed during tests that after a certain period of time the patient no longer responds well to the signals and slowly returns to his old gait. If a harder signal, or a different signal, is given every so often, the patient picks up the given cues again. This can be done passively by giving harder signals in a certain period. The system is capable of determining if there is a link between pressures on handles and walking speed. By measuring the pressure on the handles it is possible to get an impression of the position of the user or patient behind the walker. The position of the user can also be denoted as the posture or the stance of the user. For example, the user can be fed with feedback signals at a regular frequency, e.g. on the frequency of the intended gait or stance. When a deviation of the intended gait or stance may be detected, a harder or a different signal can be fed to the user to bring him back to his regular intended gait. For example, instead of a regular projected line, a vibration in the handle may be given when it is sensed that the user deviates from the projected pattern, or a more light intensive line may be projected. Alternatively and/or additionally, a different, e.g. harder cue or another cue, may be fed to the user at a random frequency, to keep the user attentive to the given regular cues.

Advantageously, the at least one stimuli generating device further comprises a light source configured to change color, brightness, or change on/off patterns or a plurality of light sources of different colors, such that the change in illumination indicates when gait, stance and/or activity irregularities are detected, absent.

Advantageously, the auditory cue can be changed in intensity, frequency, tone, and/or sound. Optionally, the auditory cue might be speech, of which the tone, intensity, voice etc. might be changeable as well. The system may then tell the user what to do through speech, using for example an automated voice or computer voice.

Advantageously, the vibration frequency and/or intensity of the tactile cue may be configured to be changed. As such a user or other individual, e.g. practitioner, may adapt the vibration frequency and/or intensity to the needs of the user or patient.

Advantageously, the proximity sensor can be fixed to the intermediate supporting frame, or to a seat/basket fixed to the intermediate supporting frame. Providing the proximity sensors in this location is ideal for measuring the position of the feet and/or legs of the users during movement.

Advantageously, the speed sensor may be configured to measure the rotating speed of one of the wheels or of both wheels. Providing a speed sensor on each wheel has the advantage that a turn or variations in wheel speed can be detected.

Advantageously, the speed sensor can be a Hall sensor or an encoder. Various sensors can be possible that can detect the speed, such as the rotational speed, of a wheel.

Advantageously, the at least one stimuli generating device further comprises a display, said display being configured to display at least one of gait, stance and/or activity information of the user as a function of time and feedback. The user can then become more aware of his improvements, and can be encouraged to adapt and modify his gait and/or stance.

The display can be mounted on the walking aid, or can be a separate display, e.g. a display of a mobile communications device, advantageously a smart device, such as a smartphone, a tablet or a smart watch. Advantageously, the display can be provided by at least one of a screen or a smartphone, a tablet or a smart watch.

Advantageously, the inertial sensor is at least one of an accelerometer, gyroscope and/or magnetometer, or other inertial sensors to detect small (angular) accelerations during each step.

Advantageously, the proximity sensor further comprises one or two cameras configured to detect at least one of step frequency, step size, step width, ground clearance, walking speed, walking distance, position of the user and/or position of the feet.

Advantageously, the proximity sensors and/or the stimuli generating devices are provided by external sensors and/or devices such as a smart device, a GPS, a pedometer, an activity tracker, a bike computer, these external devices preferably being configured to interact with the system.

Advantageously, the system is adapted for users being affected by Parkinsonism, Multiple Sclerosis, Cerebral Infraction, or for users wishing to get feedback on their stance, gait, and/or activity irregularity or for users in rehabilitation. With the user profile, the system can be adapted to any type of user.

Advantageously, the system further comprises means for connecting to an external device or network, such as via a wireless protocol such as Bluetooth, NFC, Wi-Fi, LiFi, 3G, 4G, 5G, LoRa, and/or via a cable. The system is then capable of connecting for example to a mobile communications device such as a smart device, the smart device can be used to visualize the data, analyze the data, configure the user profile, but also the visual, tactile and/or auditory cues can be generated by the smart device.

Advantageously, there can also be provided a walking aid comprising at least two wheels, two handles and a frame, wherein the frame comprises an intermediate supporting frame between the left and right handles, the walking aid further comprising the system as described in the present application.

Advantageously, there is also provided a method for retrofitting a walking aid with the system as described in the present application. Existing walking aids can thus be adapted to comprise the system of the present invention. As such, users or patients that are already acquainted to their own walking aid, can continue using their walking aid, while it is being retrofitted with the system of the present invention, and thus may helping them to improve their gait, stance and/or activity.

The invention further relates to a method for providing feedback with at least one cue to a user walking with a walking aid, the method comprising the steps of:

- storing user data, preferences and an acceptable threshold in a user profile,
- recording sensor data with a configuration of at least one sensor positioned on the walking aid while a user is moving,
- determining gait, stance and/or activity parameters from the acquired sensor data,
- comparing the measured parameters with the user data and preferences to determine if the gait, stance and/or activity parameters fall within the threshold,
- if the measured parameters are not within the acceptable threshold,
- verifying using all sensor data and user preferences to validate gait/stance irregularities, verifying the cues status, turn cue on or change cue type, intensity or rate depending on user profile and cue status, if the measured parameters are within the acceptable threshold, the gait and/or stance are considered as regular, verifying the cues status, based on the user profile preferences and cues status, determining the next cue action.

The method has the advantage that it is capable of providing more than a cue that is either 'on' or 'off'. The method is capable of providing any type of cue pattern, and any type of cue, with any type of intensity to the user. These can be alternated as a function of the needs of the user. It has been observed that the lack in different cue types and variations within one system holds several disadvantages: people can get used to their recurring cues. This habituation will minimize the effect of the trigger. The response to the repeated stimulation decreases and may cause the user to still experience gait irregularities or an incorrect posture, even while a feedback cue is triggering the user into regulated gait and/or proper posture. The present method and system is capable of varying the type, rate and/or intensity of a cue, and/or mixing the type, rate and/or intensity of a cue. For example, regular feedback signals may be mixed with feedback signals at an irregular or random frequency.

The method and system of the present invention has the advantage that it can be tailored to the needs of an individual. Especially users with progressive diseases will need different and/or different types of triggers throughout the course of their disease. The disease activity might even vary throughout the course of the day. Besides, one person's symptoms could vary from another person's symptoms. The type and intensity of the cue can be varied so as to adjust the capabilities of the system to the specific needs of an individual. Similarly, users in rehabilitation and recovery, may need different and/or different types of triggers throughout the course of their recovery. All these parameters can be adapted in the user profile.

Advantageously, the step of determining gait, stance and/or activity parameters further comprises the step of performing multi-sensor data fusion with the acquired sensor data to determine gait, stance and/or activity parameters if a plurality of sensors is used.

Advantageously, the step of determining gait, stance and/or activity parameters further comprises the step of validating a single gait, stance and/or activity characteristic with the data of multiple sensors if a plurality of sensors is used.

The method has the advantage of being able to generate in depth data about gait characteristics. A more elaborate stance and gait detection system and method that is able to combine sensor data has the advantage that indicators of stance and gait irregularities can be detected in an earlier stage. A system and method that can pro-actively prevent these stance and gait irregularities enable users to continuously optimize all aspects of their gait and posture.

Advantageously, the cue is at least one of a visual, auditory or tactile cue. The auditory cue may be a signal, such as a beep or other sound, but may be a speech signal as well.

Advantageously, the cue is generated by a stimulus generating device such as a light source, a display, an electroacoustic transducer, a vibration unit.

Advantageously, the configuration of sensors comprises at least one of a camera, a force sensor, a time sensor, a speed sensor, a position sensor, a movement sensor, an inertial sensor, an optical sensor, an ultrasonic sensor, an infrared sensor, a radiographic sensor, and a time of flight sensor.

Advantageously, the method further comprises the step of updating the user profile preferences with the measured data.

Advantageously, the method further comprises the step of giving feedback cues using gait, stance and/or activity data collected by sensors placed on a walking aid or on an external device.

Advantageously, there is also provided a computer program product comprising software which executed on one or more processing engines, performs the following steps to provide feedback with at least one cue to a user walking with a walking aid:

storing user data, preferences and an acceptable threshold in a user profile, recording sensor data with a configuration of at least one sensor positioned on the walking aid while a user is moving, determining gait, stance and/or activity parameters from the acquired sensor data, comparing the measured parameters with the user data and preferences to determine if the gait, stance and/or activity parameters fall within the threshold, if the measured parameters are not within the acceptable threshold, verifying using all sensor data and user preferences to validate gait/stance irregularities, verifying the cues status, turn cue on or change cue type, intensity or rate depending on user profile and cue status, if the measured parameters are within the acceptable threshold, the gait and/or stance are considered as regular, verifying the cues status, based on the user profile preferences and cues status, determining the next cue action.

Turning the cues off or lowering their intensity by fading them away are examples of these actions.

Further embodiments of the computer program product are defined in the dependent claims.

The computer program can be stored on a non-transitory storage medium such as an optical disk, a magnetic hard-disk, a magnetic tape, a solid state memory, or similar.

Advantageously, the system is configured to be connected to a smart device.

Advantageously, visual, tactile and/or auditory cues are generated by the smart device.

Advantageously, the user profile or a part of the user profile is configured on a smart device.

Connecting the system to a smart device has the advantage that the smart device can interact with the system. The smart device can generate the cues based on the data analysed by the system. The vibrating and/or sound signal can be generated via the smart device, such as a smartphone. Connecting the system to a smart device has the advantage that the user profile and user preferences (such as correct step frequency) can be easily modified using an "app", the measured indicators of the gait, stance and/or activity irregularities can be easily visualized by the user and/or therapist, thereby progress can easily be monitored and the user profile be adapted based on this progress.

Therefore, it is an advantage that the present invention provides an adaptive feedback system and method thereof to regulate the gait and stance of the user of a walking aid. The walking aid comprises a walker having a frame and wheels. The walking aid can be a wheeled walker. The system can be configured to give feedback to the user about the stance and/or gait, and to alternate the intensity and/or the type of feedback to continuously trigger and stimulate the user. The system selects and activates the type and intensity of the feedback triggers based on a predefined and stored user profile. The triggers can include one of or a combination of visual, auditory and/or tactile cues.

The stance, gait and/or activity irregularities of a user of a walking aid is measured via at least one sensor. When more than one sensor is used, multi-sensor data fusion is performed to provide more accurate data. This data can be collected by sensors that are placed on the walking aid and may further be supplemented by data from external devices. The fusion of sensor data advantageously lead to real time insight in the position, stance and the walking pattern of the user. Therefore the sensors may detect parameters that define characteristics of the position, stance and gait. These parameters, or indicators include but are not limited by step size, step frequency, walking speed, step height, foot position, leg position, distance between the user and the walking aid, and pressure on the walking aid.

Stimulating the user to improve the gait or stance through the use of (a combination of) cues is hereby described. Based on the gait and stance analysis the invention gives feedback to the user and guides the user towards a proper posture, position and gait. The intensity, rate and type of (the) feedback cue can be adapted by the system based on stored predefined user preference data and/or based on sensors that detect contextual and/or personal parameters, also the disease and/or rehabilitation profile of the user may be inputted in the user profile. Alterations in the type of cue and/or in the intensity may minimize habituation effects, make the invention work in all types of social and/or environmental contexts, and apply to the needs of the individual.

Further advantageous embodiments are represented in the subclaims.

Further references to the characteristics and technical contents of the present invention are made hereunder. However, the detailed descriptions and appended drawings and figures that display the disclosure are merely shown for exemplary purpose, instead of restricting the scope of the instant disclosure.

BRIEF DESCRIPTION OF THE DRAWINGS

These and other features, aspects, and advantages of the apparatus, systems and methods of the present disclosure will become better understood from the following description, appended claims, and accompanying drawing wherein:

FIG. 4 is a table illustrating which sensor type is capable of detecting which type of indicators of stance, gait and/or activity irregularities.

DEFINITIONS

Figure 1:
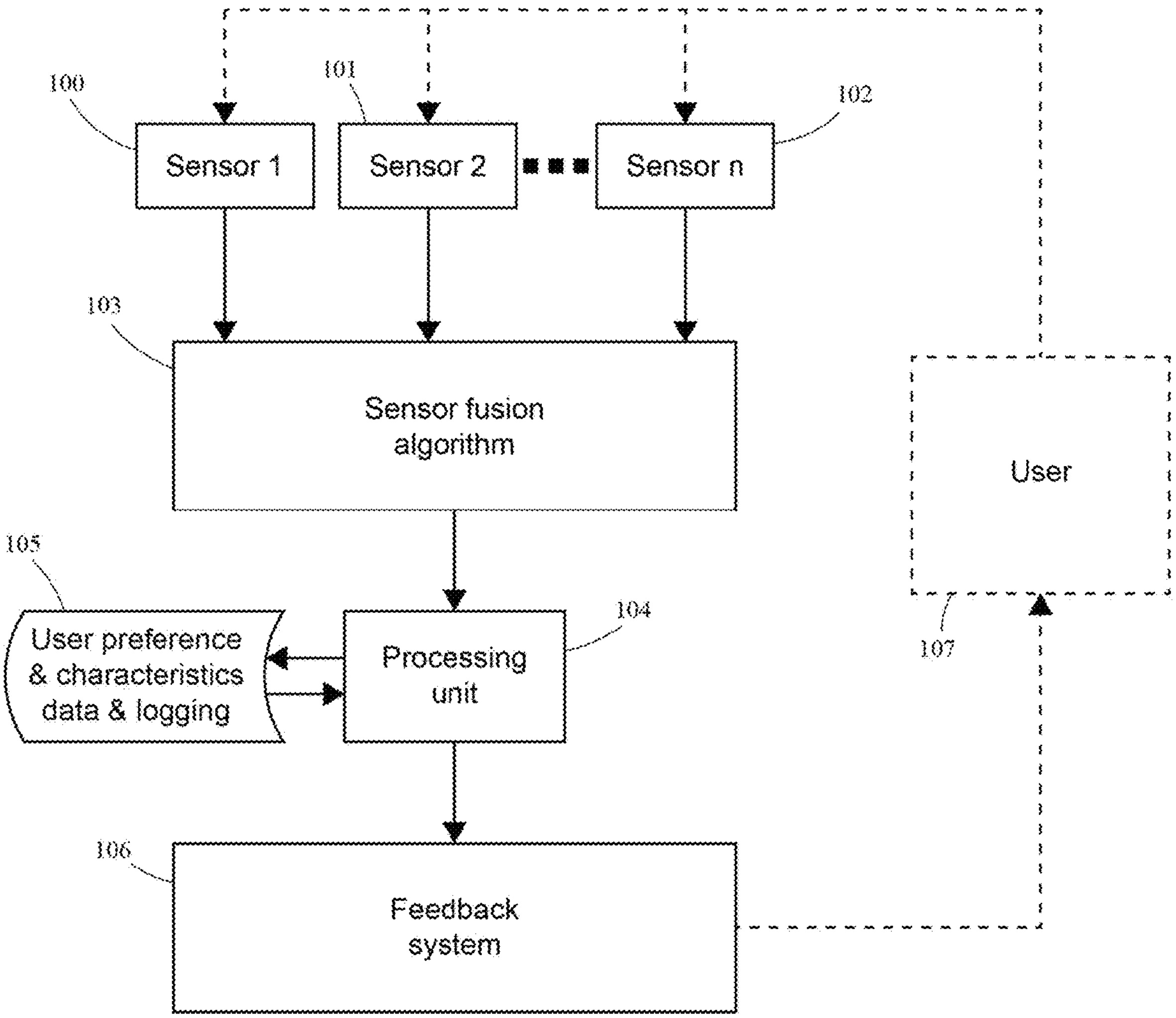
FIG. 1 is a flowchart illustrating the feedback system providing cues to the user based on sensor readings.

Gait, stance and/or activity indicators comprise at least one of the step frequency, step size, step width, ground clearance, walking speed, amount of pressure on the walking aid, the ground contact forces of the feet, and toe-to-heel walking. Step size or step length is considered to be the distance between the feet measured in the sagittal plane, or in a plane parallel thereto. Step width is considered to be the distance between the feet measured in the frontal plane, or in a plane parallel thereto. Stance is considered to be the position or attitude of a person standing.

A stimuli generating device is a device for generating at least one of a tactile, visual or auditory cue to the user. User gait, stance and/or activity characteristics are the actual gait, stance and/or activity indicators of the user.

Gait, stance and/or activity irregularities are gait, stance and/or activity of a user which depart above or below a certain threshold from the user's gait, stance and/or activity characteristics.

A smart device is an electronic device such as a smart phone, a smart watch, a tablet, etc. It can be connected to other devices or networks via different wireless protocols such as Bluetooth, NFC, Wi-Fi, LiFi, 3G, 4G, 5G, LoRa, etc., that can operate to some extent interactively and autonomously. It can be a mobile communications device.

DESCRIPTION OF EMBODIMENTS

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The present disclosure is focusing on a system and a method thereof that can continuously regulate gait, posture and activity of users of a walking aid.

This gait, posture and activity regulation may be beneficial for ones with movement disorders, potentially as a consequence of a disease like Parkinsonism, Multiple Sclerosis, or a cerebral infarction. Ones with movement disorders such as these but not limited by the aforementioned may experience difficulties in maintaining a constant gait and/or proper stance. This may result in a varying or decreasing step size, a decrease or increase in step frequency, decreased lift height of the feet, and/or a change in position of the user relative to the walking aid. The gait characteristics of a regular or an irregular gait can vary for each of the movement disorders and for each individual.

FIG. 1 is a flowchart illustrating a method for regulating the gait, stance and/or activity irregularities of a user. The varieties in gait, stance and/or activities can be detected using one or more type of sensors or type of sensors 100, 101, and 102 that can be placed on the walking aid. Additional external sensors and/or devices can also be provided to the system, for example via a smart device.

At least one sensor is used to measure gait, stance and/or activity irregularities. At least one speed sensor is capable of detecting when a user stops walking. The feedback system will be triggered in this case. However, when more sensors are being used, e.g. a pressure sensor in the handles which are capable of detecting irregularities in pressure during such a stop, the system can better distinguish if this was an intended stop or a FOG. Therefore a plurality of sensor types may provide a more robust system.

Based on multi-sensor data fusion 103, the processing unit will determine 104 whether the gait, stance and/or activity of the individual can be considered as regular or as irregular using a stored user profile 105.

Combining sensor data may allow to sense early indicators of stance and gait irregularities. This could, for example, benefit to the prevention of a 'Freeze of Gait' (FOG). A system that can pro-actively detect and react upon early stance and/or gait irregularities will enable users to continuously optimize their gait and/or posture and may reduce the chance of gait or stance irregularities developing into more severe states or conditions, such as a FOG. Having information about the stance and/or gait characteristics and giving feedback to the user could therefore be valuable in preventing or slowing down the progression of a disease, or benefit in the effectiveness of medical rehabilitation therapy.

When gait, stance and/or activity irregularities are detected, because of the feedback system, a cue is generated to incite the user 107 to improve his gait, stance and/or activity. The cue can be (a combination of) visual, auditory and/or tactile feedback cues 106. The cue is generated by a stimulus generating device such as a light source, a speaker, a vibration unit, etc. Alternatively and/or additionally, the cue may be generated to the user at the frequency of the regular activity, e.g. at the intended gait or stance. When a deviation from the intended regular activity is sensed, an irregular cue may be generated to bring the user back to the intended regular activity. The irregular cue may be irregular in frequency, hardness and/or type of cue. The irregular cue may also be generated random, as to keep the attentiveness of the user, advantageously without waiting until a degeneration of the activity is sensed. As such a 'surprise' effect may be reached with the user which may result in keeping the user focused on the activity, and which may avoid the user in developing irregularities in that activity requiring a feedback signal. Of course, variations and/or mixture in feedback cues may be possible.

The components that generate the feedback cues are held by the walking aid or are placed in an external device, such as a smart device, e.g. a smartphone, a tablet, a smart watch, etc. that shows gait data and/or walking distance for example. The method is capable of determining the rate, type and/or intensity of the feedback cues, as explained in reference to FIG. 3.

In an example, the stimulus generating device comprises a light source fixed to the frame of the walking aid and which is able of creating a visual projection of a line on the ground plane.

The stimulus generating device may also comprise a speaker or other device capable of producing hearable sound to provide an array of tones of which the rhythm and tone height can be changed based on the user's preferences. The speaker or electroacoustic transducer can also be configured to produce a periodic or rhythmic sound, wherein preferably the period or rhythm is related to the step frequency.

The audio feedback could also be provided by a headphone or earphones connected to the system. The loud beeps might be annoying in some contexts. This can be solved by including a headphone jack/or a system that allows connecting headphones wirelessly. If a headphone jack is used, the preferred location may be in one of the handles.

The stimulus generating device may also generate a tactile feedback cue with a vibration unit. The vibration unit can be provided in the handles of the walking aid.

The stimulus generating device may also generate a visual cue with a screen fixed to the frame or part of another device, e.g. a smartphone, capable of displaying the measured gait, stance and activity information and feedback. The screen can be provided by an external device such as a smartphone, or a tablet, or even a smartwatch. The stimulus generating device may also provide a visual cue with at least one light source capable of changing color, brightness, or changing on/off patterns, or a plurality of light sources of different colors, such that a different color is displayed when gait, stance or activity irregularities are detected or absent. Alterations in the type of cue and/or in the intensity may minimize habituation effects, make the invention work in all types of social and environmental contexts, and/or apply to the needs of the individual.

Both the decision making process that determines whether gait and/or stance irregularities took place and the intensity, rate and type of feedback cue can be configured to meet the needs and wants of an individual through a stored user profile, see FIG. 1. This user profile can hold information about personal gait, stance and activity preferences, indicators of gait, and/or stance irregularity, and preferences about feedback cue intensity, rate and type.

The user profile can therefore be particularly adapted to the user, to his condition, the evolution of his illness, to the particular needs of the user.

Figure 2:
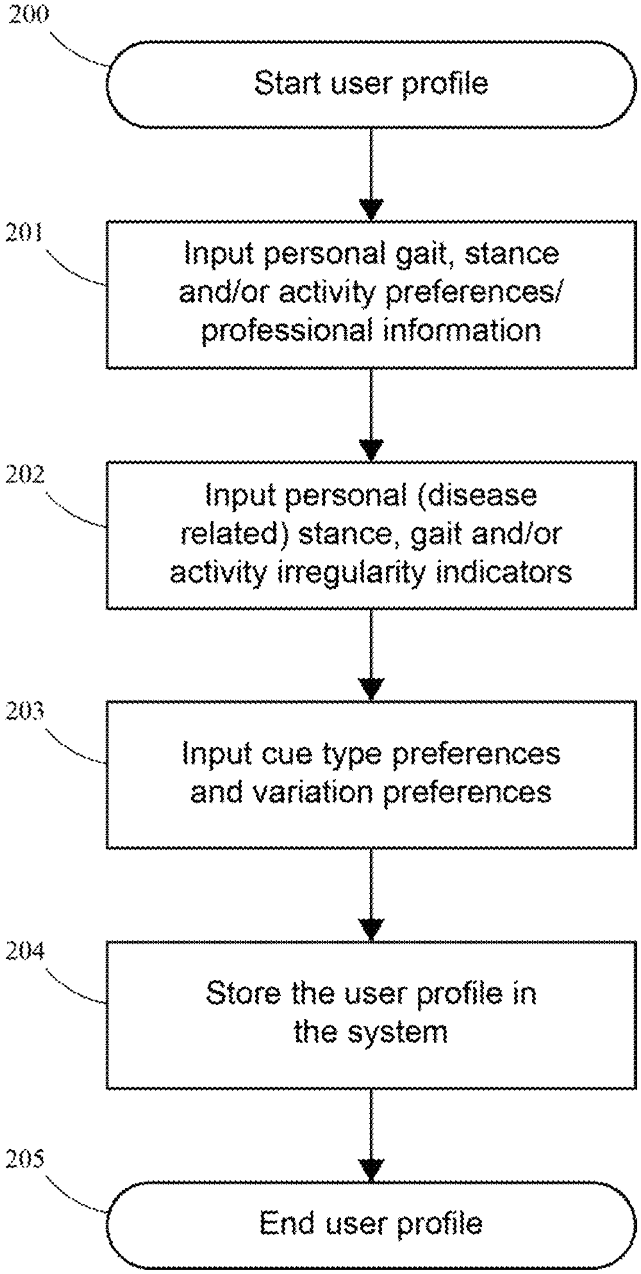
FIG. 2 is a flowchart illustrating how data is stored in the user profile of the system.

FIG. 2 is a flow chart illustrating the preferred procedure and order to store the user profile in the system. First the personal gait, activity and stance preferences can be filled in 201. Examples of these preferences may include but are not limited to the user's preferred step size and step frequency. The gait, stance and/or activity characteristics can be characterized by the following indicators: step frequency, step size, step width, ground clearance, walking speed, walking distance, user's position relative to the walking aid, position of the feet, amount of pressure on the walking aid, ground contact forces of the feet, toe-to-heel walking. All the indicators may not be required, but the more indicators are measured, the better the assessment of the gait, stance and/or activity of the user can be made.

The following indicators are preferably measured: step frequency, step size, walking speed, amount of pressure on the walking aid.

Afterwards, the system allows to input personal, e.g. disease related or rehabilitation related, stance and/or gait irregularity indicators 202. This tells the system when a type of gait can be considered as irregular, and therefore when the feedback system can be activated. This feature could be used to spot indicators of disease related gaits and/or posture, but could also be used to train specific gait and/or posture aspects in medical rehabilitation therapy.

As a third step the system allows to input the preferred type of feedback cue and preferred variations in the rate and intensity of these cues 203. The cue preference can differ widely per individual. E.g. some users might need a direct cue, like ones with Parkinsonism who could need constantly recurring triggers to prevent a FOG, while other users will benefit more from indirect feedback about their progression, like medical rehabilitation patients. As a last step the user profile data will be stored in the system 204. The personal gait, activity and/or stance characteristics, the irregularity indicators and preferred cue(s) could be stored by the user, by an expert and/or caregiver before first use, and/or could be stored or changed afterwards. Having the preferred user characteristics allows configuring each system to be well-tailored to the user's needs and wants. This will allow the invention to be usable for a large variety of users with varying motor abilities and/or diseases.

Apart from the data in the aforementioned user profile, stance, activity and gait data can be stored during use as well. From the recorded data, statistics can be made and stored in the user profile. This logged data may help in finding gait, stance and/or activity patterns that develop during a longer period of time and will allow users and other stakeholders to gain insight in the progression over time. The decision making process of the invention could utilize both the preset characteristics and the logged sensor data to control the feedback system. Combining the stored data comprising the preferred and logged data and comparing this to the real time measurements of the multi sensor data fusion can highlight irregularities in stance and/or gait.

The personal gait, activity, stance characteristics and the irregularity indicators can be updated during use as well, in particular for medical rehabilitation patients, who can show quick progress in gait, activity and stance improvements. Therefore, a method for monitoring the progress in rehabilitation patients can also be provided by the present invention. This provides a very useful tool to the practitioner who has technical data recorded with the system while the patient is moving. This recorded technical data shows the evolution of the recovery of the patient over time.

Figure 3:
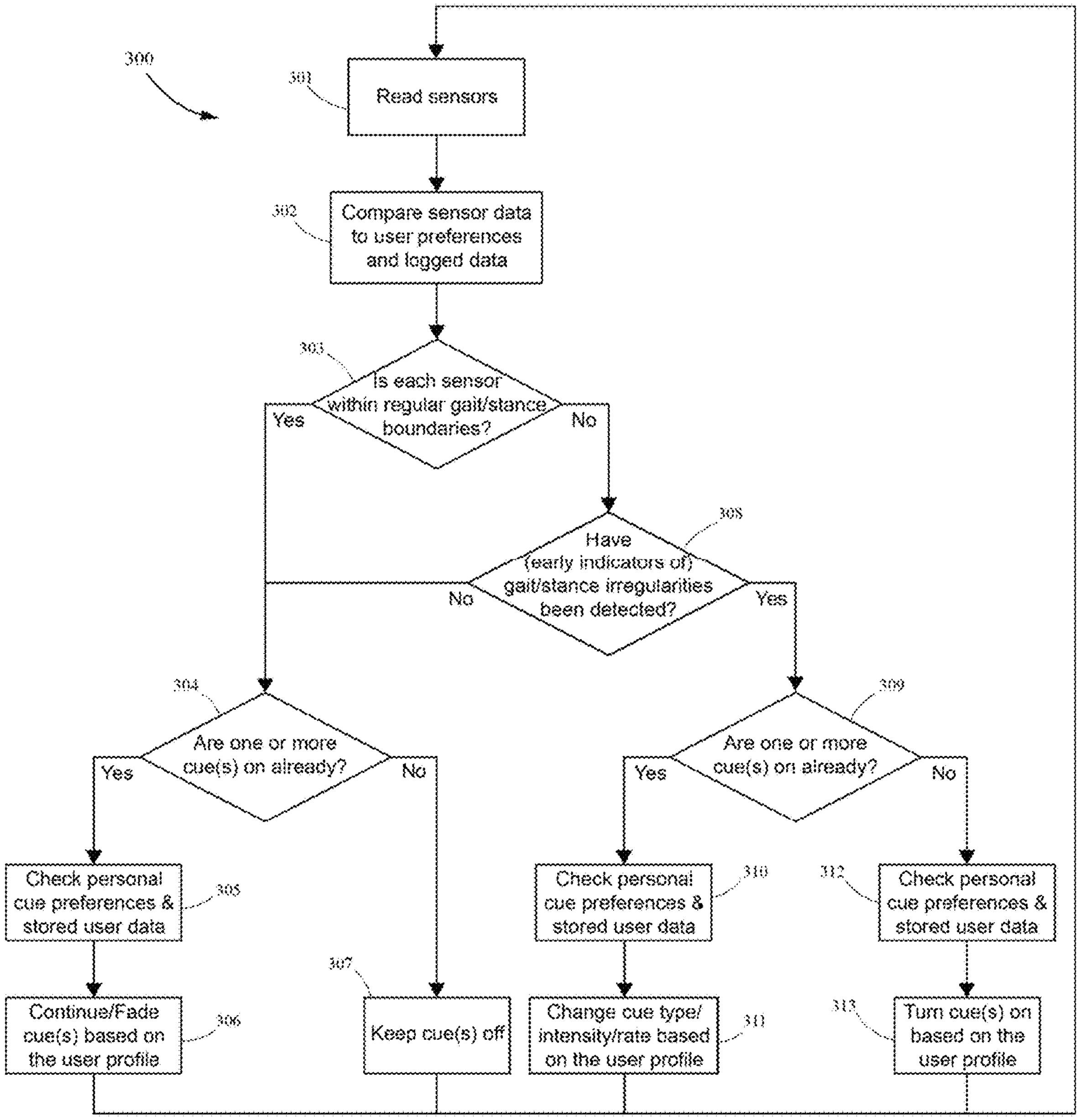
FIG. 3 is a flowchart illustrating how the method generates cues to the user based on the sensor readings.

FIG. 3 shows a flowchart illustrating a method of giving feedback cues to a user using gait, stance and/or activity irregularities data collected by sensors placed on a walking aid. Additional sensors might be provided by an external device, such as a smart device, or e.g. sensors applied to the patient, or otherwise. The described method might be executed by a microcontroller that is fixed to the frame of the walking aid. Stance, gait and activity irregularities are measured with a configuration of sensors installed on the walking aid, while the user is moving.

The microcontroller first reads sensor data 301 recorded by the configuration of sensors on the walking aid. The microcontroller performs sensor data fusion to deduce gait, stance and/or activity irregularities characteristics. Data from multiple sensors is combined to detect the gait, stance and activity patterns. Analyzing the patterns can show gait, stance and/or activity irregularities.

For example, after the sensor data is collected 301, these values are verified by cross checking, e.g. variances in handle pressure and wheel speed can show patterns from which step frequency can be deducted. This information will further be used to validate the measured step frequency. Noise can be reduced as well during this step, for example with the use of a Kalman filter. Therefore, data fusion is used in two ways: (1) data from multiple sensors is combined to detect complete gait and stance patterns, and (2) multiple sensors are used to validate single gait characteristics.

The controller compares the measured characteristics to the user profile and logged data 302 to see if the measurements fall within a predefined acceptable threshold 303 that is stored in the user profile.

For example, the detected step frequency is compared to a stored ideal frequency. If these values differ too much for a user this will be considered as a gait irregularity. This decision will be based on preset stored user characteristics in the user profile, e.g. minimum and maximum values stored by a physiotherapist and logged data, e.g. if the system recognizes a gait pattern that has resulted in a Freeze of Gait earlier.

If all sensor readings are within regular boundaries, and the gait and/or stance can therefore be considered as regular, the controller checks the status of the feedback cues 304. Based on the preferences or needs of the user 305 the system can determine the proper cue action 306.

If one or more sensor readings do not fall within a predefined acceptable threshold, this might highlight gait or stance imperfections. But such a reading, which is outside an acceptable threshold, might also be caused by faulty sensor reads or contextual disturbances. E.g. when a user with Parkinsonism willingly slows down to stop in front of a red traffic light, the system should not see this as an early indicator of a FOG. To be sure the microcontroller only triggers the feedback system for gait and/or stance irregularities, other sensor values, logged data and/or the user profile should validate possible gait and/or stance irregularities 308. Only when these irregularities are detected the system should turn cues on 313, change the cue type and/or the cue intensity or rate 311. The severity of the action and cue selection could be based on the personal cue preference (310, 312) and the gait irregularity indicators. If a gait or stance severely differs from optimal, the user might need more intense feedback, while a minor irregularity may be solved with a minor cue.

For example, when the system checks if an activated cue results in an improvement of gait/stance patterns. If improvement is detected, the cue could start fading away 306, while the cue could get more intense when gait irregularities become more severe 311. Even if a more intense cue does not result in improved gait, another type of cue will be used by the system, possibly along with the apparent cue.

It is to be noted that the diagram of FIG. 3 illustrates the most general feedback system. Additional gait, stance and/or irregularity indicators and/or appropriate feedback cues can be provided to the diagram. A large number of use cases can be envisaged with the system of the present invention to improve the gait, stance and/or activity irregularities of a user, which use cases can be particularly adapted to the user and to the evolution of his condition. E.g. some users suffering from Parkinsonism could have difficulties in executing multiple tasks at the same time. While a given cue could result in a proper gait for this user, it will be mentally exhausting to continuously having to process the cue. For this type of user, a system can be beneficial that gives cues on a low intensity and that cues quickly fade away when a regular gait is achieved. On the other hand, ones with Parkinsonism who do not have difficulties in processing the cues while walking could benefit from continuous and high intensity cue types. Since this will help them in continuous gait regulation. Again, the preferred cue types could differ and could be set to match the needs and wants of an individual. A user suffering from Parkinson's disease could benefit from a projected laser line on the floor, while this cue will be useless for one with a CVA. On top of that the system can learn which cues, rates and intensities are effective for specific situations using the logged data.

FIG. 4 is a table which illustrates the various types of indicators of stance, gait and/or activity irregularities and which external devices are capable of measuring each of these. Indicators of these irregularities as shown in FIG. 4 could be the step frequency 401, step size 402, step width 403, ground clearance 404, walking speed 405, amount of pressure on the walking aid 409, the ground contact forces of the feet 410, and toe-to-heel walking 411, instead of a regular gait where the heel touches the ground first and the toes afterwards. The ground clearance is the distance from the bottom of the person's feet to the ground. During a proper gait the feet need to come loose from the ground during the swing phase.

The various types of sensors are A camera, B force sensor, C time sensor, D speed sensor, E position sensor, F movement sensor, G inertial sensor, H optical sensor, I ultrasonic sensor, J infrared sensor and K radiographic sensor. A time of flight sensor, or LIDAR may also be used.

At least one sensor can be used in the sensor configuration of the system. At least a speed sensor to detect the walking speed and the step frequency. A single sensor/measurement could already be sufficient for the detection of gait irregularity indicators. The more different indicators are being sensed, the more false positive measurements can be filtered out.

Each of the indicators shown in the table of FIG. 4 can hold valuable information for medical specialists. On top of that, the list of indicators has been created along with these experts. At this moment, these gait indicators are used by specialists to assess the progression of Parkinson's disease during a consult. So the more information will be logged when the system is in use, the better these specialists will be able to assess the status of the patient. Some patients could for example start compensating their gait inabilities. This could result in a proper step size and frequency, but an odd step width. Monitoring the progression of all or some of these indicators provides valuable information to the medical specialist.

The present invention does not depend on the type of walking aid/wheeled walker which is used, but on the configuration of the sensors provided on the walking aid/wheeled walker. The walking aid shown in the FIGS. 5, 6 and 7 are shown for clarity purposes.

Figure 5:
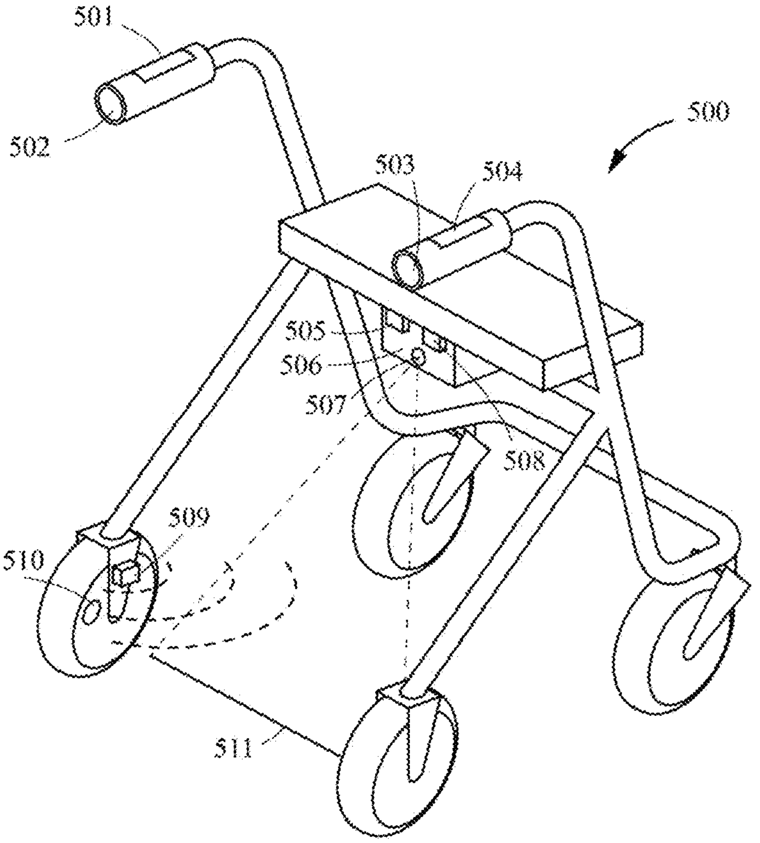
FIG. 5 shows a perspective view of a walking aid provided with the system comprising a configuration of sensors and stimulus generating devices such as a light source.
Figure 6:
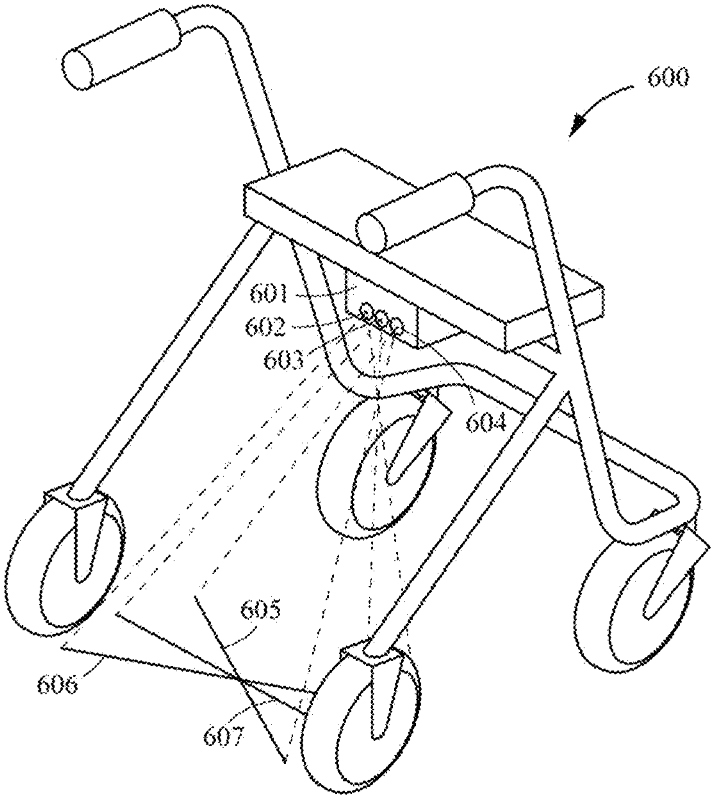
FIG. 6 shows a perspective view of a walking aid provided with the system comprising a configuration of sensors and stimulus generating devices such as three light sources.
Figure 7:
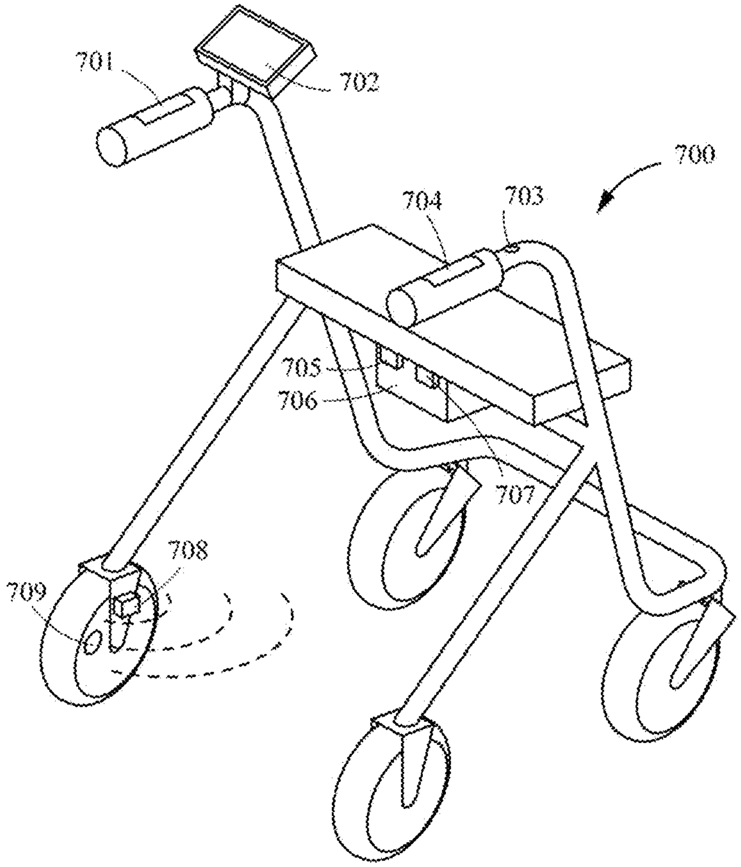
FIG. 7 shows a perspective view of a walking aid provided with the system comprising a configuration of sensors and stimulus generating devices such as a display.

As most walking aids, the walking aid illustrated in FIGS. 5, 6 and 7 comprises a frame provided with a set of rear wheels and a set of handles. It may further comprise one or two front wheels. The portion of the frame which connects the left portion of the frame, i.e. left wheels and left handle and right portion of the frame, i.e. right wheels and right handle is hereby called the intermediate supporting frame. The intermediate supporting frame can be used to install devices or sensors, but also the control unit. Furthermore, a seat can be installed on the intermediate supporting frame such that the user can rest, or a basket for carrying items. In this case, the control unit and some devices and/or sensors can be fixed to the seat or to the basket.

The various sensor configurations and/or stimuli generating devices described in the following examples can be combined. The configurations which are provided to the walking aid depend mostly on the patient's condition.

FIG. 5 illustrates an example of a walking aid particularly adapted to users affected by Parkinsonism or a comparable extrapyramidal disorder. As mentioned, patients with these types of disorders can experience gait irregularities, stride reduction and/or a FOG.

In this embodiment at least one proximity sensor, e.g./Ultrasonic and/or J Infrared is preferred that is capable to detect the step frequency 401 and the step size 402. Optionally, the step width 403 and ground clearance 404 can also be measured. The proximity sensor can also be provided by a time of flight sensor or camera, or LIDAR sensor.

A possible sensor configuration that can be provided on the walking aid is hereby described. The configuration of the stimulus generating devices is also described. The processing unit can also be fixed to the frame, and more preferably to the intermediate supporting frame.

In this example, the proximity sensor(s) is/are fixed to the frame of the walking aid. The proximity sensor(s) is/are aimed directly at relevant parts of the user's body, or aimed in a direction where a part of the user's body could be while using the system. In the example shown, the proximity sensors are provided on the intermediate supporting frame or installed on the seat/basket, such that during use, the sensors are located in front of the user, such as at locations 505, 508, 509.

When the user starts moving, the sensor(s) is/are capable to detect a change in distance between the user's body and the sensor(s). Multiple measurements can be used to generate patterns and give continuous indications of the location of the user's body parts, such as the legs and/or feet of the user. This information can be used to measure the step frequency 401 and the step size 402, and could also measure the step width 403 and ground clearance 404.

Walking speed 405 is preferably detected by a speed sensor. For example, a speed sensor D comprising a Hall Effect sensor fixed to the frame and a magnet fixed to a spoke of at least one of the wheels 510 can be used. Other types of sensors known to the skilled person can also be used for measuring the walking speed.

A force sensor B is preferred for detecting the amount of pressure on the walking aid 409, the ground contact forces of the feet 410, and/or the toc-to-heel walking 411. As described above, the force sensor can be useful for detecting indicators of a Freeze of Gait. For example, the force sensor can be useful for detecting balance and/or balance problems, which correlate with differences in step size, step width and/or frequency. As such, the force sensor may detect indicators for a FOG.

The preferred location of the force sensors 501, 504 for detecting the amount of pressure on the walking aid 409 is in or near both handles of the walking aid. In the example of FIG. 5, the force sensors 501, 504 are provided on the handles, such that the force sensors are in a proximity of where the hands of the user take support during use of the device.

Indicators for the ground contact forces of the feet 410, and/or the toe-to-heel walking 411 are preferably detected by an external device, as defined in the table of FIG. 4.

The feedback cues in this embodiment comprise at least one of the following:

at least a light source 507 fixed to the frame which is able to create a visual projection of a line 511 on the ground plane perpendicular to the direction of motion such that users can step over it, e.g. when experiencing a FOG or when being aided to help keeping a regular stance and/or gait, and/or a speaker or other device capable of producing hearable sound to provide an array of tones of which the rhythm and tone height can be changed based on the user's preferences, and/or a vibration unit 502, 503 in the handles of the walking aid of which the intensity and rhythm can be varied.

FIG. 6 illustrates another implementation of the embodiment above, wherein one of the preferred feedback cues comprises at least three light sources fixed to the frame of the walking aid.

The three light sources can also be fixed under the seat or basket of the walking aid. Each of the light sources 602, 603, 604 is able to create a visual projection of a line on the ground. One of the light sources projects a "move forward" line 607 which is perpendicular to the direction of travel of the walker in front of the feet of the user, when the user moves forward. The other light sources project "turn right" 605 and "turn left" 606 on the ground angularly offset from the center of the "move forward" line. The "turn right" 605 line is oriented towards the right such that it helps the user turn right, and the "turn left" line 606 is oriented towards the left such that it helps the user turn left. The system may allow the user to change the angular offset between −45 and 45 degrees for example in the configuration settings. The angular offset may correspond to the maximum angle between the 'move forward' line and the 'turn left/right' lines.

The projected lines that are not perpendicular to the initial direction of travel should help the user to initiate a corner. The user can activate the projection of the "turn left" 606 or "turn right" 605 lines respectively with a left or right switch for example provided on the handles of the walking aid.

With the gathered sensor data, the system is capable of detecting a corner after it has been initiated. For example, when there might be a speed sensor on a left wheel and on the corresponding right wheel of the walking aid, and the system detects a different speed on each of the wheels, the system might detect a corner or a bent, that might have been initiated by the user. Alternatively and/or additionally, the user may initiate a bent or curve or corner by pressing a button placed on the handle. Two buttons are installed on the prototype, one on each handle. If the user presses the right button, the line that is slanted to the right lights up. And, similarly, if the user presses the left button, the line that is slanted to the left lights up.

Instead of three light sources, a single light source can be configured to rotate upon activation by the user, when he decides to turn left or right so as to generate a projected line having the desired orientation and thereby to assist the user in making a turn. The direction of the line can be controlled by the shift but also the angle, for example in a range of 0 to 45°.

The inventors have observed that the projection of these oblique lines has a favorable effect when the user decides to make a turn.

The light source is preferably a laser light source.

FIG. 7 illustrates another example of a walking aid. This example is particularly adapted for users with Multiple Sclerosis. As mentioned, ones with Multiple Sclerosis can experience gait dysfunctions throughout the course of their disease. This may have effect on the walking velocity, stride length, and cadence of patients. Indicators that might highlight these irregularities comprise step frequency 401, step size 402, step width 403, ground clearance 404, walking speed 405, position of the feet 408, and/or pressure on the walking aid 409.

In this embodiment at least one proximity sensor, e.g. I and/or J is preferred that is capable to detect the step frequency 401 and the step size 402. The step width 403, ground clearance 404, and/or position of the feet 408 can preferably also be measured.

As for the examples described above, the proximity sensor(s) is/are fixed to the frame of the walking aid and aimed directly at relevant parts of the user's body, or aimed in a direction where a part of the user's body could be while using the system such as 705, 707, 708. The proximity sensors are preferably installed on the intermediate supporting frame, or under the seat/basket.

When the user starts moving, the sensor(s) is/are capable to detect a change in distance between the user's body and the sensor(s). Multiple measurements can be used to generate patterns and give continuous indications of the location of the user's body parts, such as the legs and/or feet of the user. This information can be used to find step frequency 401 and the step size 402. Preferably, step width 403, ground clearance 404, and the position of the feet 408 can also be measured.

Walking speed 405 is preferably detected by a speed sensor D compromising a Hall Effect sensor fixed to the frame and a magnet fixed to a spoke of at least one of the wheels 709.

A force sensor B is preferred for detecting the pressure on the walking aid 409. The preferred location of the force sensors that detect 409 is in or near both handles of the walking aid as shown by 701 and 704.

The preferred feedback cues in this embodiment comprise a speaker or other device capable of producing hearable sound to provide an array of tones of which the rhythm and tone height can be changed based on the user's preferences, which could be used in rhythmic audio therapy, and/or a screen 702 fixed to the frame or part of another device, e.g. a smartphone, able to display gait, stance and/or activity information and feedback, and/or at least one light source 703 capable of changing color, brightness, or changing on/off patterns when gait, stance or activity irregularities are detected or absent. The light source can also be provided by a plurality of light sources of different colors. This embodiment could be beneficial in, e.g. rhythmic, training programs in which the feedback cues can be configured to respond to specific gait, stance and/or activity aspects.

In another embodiment the invention is optimized for a user with a Cerebral Infarction. As a result of a Cerebral Infarction ones might experience decreased walking speed, short and/or uneven step and stride lengths, increased stride width, increased double support phase and/or dependence on support through the hands. Indicators that might highlight these irregularities comprise step frequency 401, step size 402, step width 403, ground clearance 404, walking speed 405, position of the feet 408, and/or pressure on the walking aid 409. In this embodiment at least one proximity sensor, e.g. I and/or J is preferred that is capable to detect step frequency 401 and step size 402, but also step width 403, ground clearance 404 and/or position of the feet 408.

The proximity sensor(s) is/are fixed to the frame of the walking aid and aimed directly at relevant parts of the user's body, or aimed in a direction where a part of the user's body could be while using the system such as 705, 707, 708. The proximity sensors are preferably installed on the intermediate supporting frame.

When the user starts moving, the sensor(s) is/are capable to detect a change in distance between the user's body and the sensor(s). Multiple measurements can be used to generate patterns and give continuous indications of the location of the user's body parts. This information can be used to find step frequency 401 and step size 402, but also step width 403, ground clearance 404 and/or position of the feet 408.

Walking speed 405 is preferably detected by a speed sensor D compromising a Hall Effect sensor fixed to the frame and a magnet fixed to a spoke of at least one of the wheels 709.

A force sensor B is preferred for detecting 409. The preferred location of the force sensors that detect 409 is in or near both handles of the walking aid as shown by 701 and 704.

Feedback cues in this embodiment preferably comprise a screen, such as screen 702, fixed to the frame or part of another device, e.g. a smartphone, able to display gait, stance and activity information and feedback, and/or at least one light source 703 capable of changing color, brightness, or changing on/off patterns when gait, stance or activity irregularities are detected or absent. This embodiment could be beneficial in training programs in which the feedback cues can be configured to respond to specific gait, stance or activity aspects. It can be very beneficial to provide the user and/or others exact numeric information about the situation and progress of the user.

In another embodiment the invention is not specifically optimized for a user with a disease or condition. Such a device can be helpful for people that want to improve their stance, gait and/or activity in general to maintain or train their mobility. It will provide the users with an additional kind of feedback about parameters of choice and can help in reaching activity goals.

While such an embodiment is not optimized for a user with a specific disease or condition, one with a disease or condition might still benefit from the advantages. E.g. people that need to become more and more active after a hip replacement or people in the early stages of dementia.

In this embodiment the system could be able to detect at least one of step frequency 401, step size 402, step width 403, ground clearance 404, walking speed 405, walking distance 406, position of the user 407, position of the feet 408, and/or pressure on the walking aid 409. 401, 402, 403, 404, 407 and 408 are preferably detected by a proximity sensor such as I or J.

The proximity sensor(s) is/are fixed to the frame of the walking aid and aimed directly at relevant parts of the user's body, or aimed in a direction where a part of the user's body could be while using the system such as 705, 707, 708.

Walking speed 405 and walking distance 406 are preferably detected by a speed sensor D such as a Hall Effect sensor fixed to the frame and a magnet fixed to a spoke of at least one of the wheels 709.

A force sensor B is preferred for detecting the pressure 409. The preferred location of the force sensors that detect the pressure 409 is in or near both handles of the walking aid as shown by 701 and 704.

The system could allow storing activity, stance and/or goals and will give feedback about the progression, for example this can be done via an app on a smartphone or an electronic platform.

The feedback cues can include a screen fixed to the frame, such as screen 702, or part of another device, e.g. a smartphone, able to display gait, stance and activity information and feedback, and/or at least one light source capable of changing color when gait, stance or activity irregularities are detected or absent, such as lamp 703.

The system described in the various examples can also be used with a smartphone app, which app is configured to communicate with the processing unit. The app can be used to configure the user profile, and select for example the personal gait, stance and activity preferences, indicators of gait, and/or stance irregularity, and preferences about feedback cue intensity, rate and type. The app can also be used to visualize the data which is collected by the various sensors and analyzed by the processing unit. The evolution of the stance, gait, and/or activity irregularities can therefore be visualized on the app, by the user and/or by a therapist. The app can therefore be used to monitor the evolution of the patient's condition and take necessary actions, by adapting in the user profile personal preferences for example.

The user profile in the app can also be automatically updated based on the large number of data and measurements which are available. The following types of sensors, configurations and stimuli generating devices types and configurations can be used for the various examples described.

The sensor configured to detect step frequency 401 can also be provided by an inertial measurement unit to be fixed to the frame of the walking aid. This inertial measurement unit could utilize an accelerometer, gyroscope and/or magnetometer, or other inertial sensors to detect small (angular) accelerations during each step. This inertial measurement unit might be used together with other sensors to detect the step size.

The sensor which is configured to detect at least one of step frequency 401, step size 402, step width 403, ground clearance 404, walking speed 405, walking distance 406, position of the user 407 and/or position of the feet 408 can be provided by at least one camera fixed to the frame of the walking aid.

The camera is aimed directly at relevant parts of the user's body, or aimed in a direction where a part of the user's body could be while using the system. The camera might record within the visual spectrum of humans or outside this spectrum, e.g. an infrared camera. Two cameras can also be used to create 3 dimensional data.

The sensor which is configured to detect step frequency 401 can also be provided by a force sensor placed in or around at least one of the handles of the walking aid. The pressure on the handle will vary throughout a step. Detecting this pressure will allow to find the frequency in which the user is walking. This force sensor might be used in combination with other sensors to detect the step size. The force sensor or pressure sensor can be provided with strain gauges in a full Wheatstone bridge configuration. These strain gauges are configured to measure the downwards forces that the user generates by pushing/resting hands on the handle.

Furthermore, positional data can be provided by a GPS unit fixed to the frame or part of a device outside the scope of the invention to detect walking speed 405 and distance 406. Furthermore, such a GPS unit allows creating training programs that involve walking a specific route and could navigate users around this route. The horizontal lines projected by the at least three light sources, as described in reference to FIG. 6, can also be used to guide the users, using the GPS data.

The system, sensors and feedback cues could be used in combination with and/or could be fully or partially replaced by systems or devices external to the walking aid. By allowing the feedback, thresholds, parameters, characteristics etc. to be varied, adjusted and/or adapted to user specific needs, an adaptive system is provided that may help the user to improve, monitor, regulate and/or train its gait, stance and/or activity.

System for providing feedback to a user of a walking aid to regulate his gait, stance and/or activity irregularities, the system being configured to be installed on a walking aid comprising a frame, at least two wheels, two handles and wherein the frame comprises an intermediate supporting frame between the left and right handles of the frame, the system comprising a configuration of sensors for measuring at least one gait, stance and/or activity indicator, a user profile comprising user gait, stance and/or activity characteristics, a configuration of at least one stimuli generating device configured to provide feedback to the user with at least one of a tactile, visual or auditory cue based on the measurements of the sensors and on the user profile.

The control unit is preferably mounted within the intermediate supporting frame. Some walking aids are provided with a seat provided on the intermediate supporting frame, the control unit can then be installed hanging under a seat of the walker. The placement and shape of the box do not obstruct the current functionality of the walker, e.g. collapsing or allowing the user to sit. Since the box is small enough and placed under the seat, the user will not bump into it while walking.

Preferably, almost all components that allow operating the control unit are placed in a proximity of the box. These components are located on the side of the control unit that is pointed towards the user. These include an on/off button, a charging port, an on/off indicator and feedback light about the remaining battery load. Two buttons that control the 'turn left/right' laser lines are placed on the handles. These are the only buttons that are not located on the control unit. It is also possible to provide some or more of these components near the handles to improve the case of operability.

Inside the box, a battery cell and/or a PCB, which may comprise a piezoelectric buzzer placed directly on the board, can be fixed. The light sources can also be provided inside the box. The piezoelectric buzzer may provide the auditory feedback cues and the laser lights provide the visual feedback cues for Parkinson's patients. The PCB has preferably a wired connection to both of the handles and to each of the sensors that are placed on the walker.

The data acquired by the sensors, the user profile, and the analyzed data etc. can also be stored on a cloud or on a network. The data could then also be accessible via a platform on the internet for example, wherein user profile could also be configured.

Software may be implemented as a computer program product which has been compiled for a processing engine to carry out any of the methods of the present invention or is compiled to execute in an interpretative virtual machine such as the Java™ Virtual Machine.

The computer program product may be stored on a non-transitory signal storage medium such as an optical disk (CD-ROM or DVD-ROM), a digital magnetic tape, a magnetic disk, a solid state memory such as a USB flash memory, a ROM, etc.

The software can be embodied in a computer program product adapted to carry out at least one of the following functions when the software is loaded onto the respective display or displays and executed on one or more processing engines such as microprocessors, ASIC's, FPGA's etc.:

storing user data, preferences and an acceptable threshold in a user profile, recording sensor data with a configuration of at least one sensor positioned on the walking aid while a user is moving, determining gait, stance and/or activity parameters from the acquired sensor data, comparing the measured parameters with the user data and preferences to determine if the gait, stance and/or activity parameters fall within the threshold, if the measured parameters are not within the acceptable threshold, verifying using all sensor data and user preferences to validate gait/stance irregularities, verifying the cues status, turn cue on or change cue type, intensity or rate depending on user profile and cue status, if the measured parameters are within the acceptable threshold, the gait and/or stance are considered as regular, verifying the cues status, based on the user profile preferences and cues status, determining the next cue action.

The software can be embodied in a computer program product adapted to carry out at least one of the following functions when the software is loaded onto the respective display or displays and executed on one or more processing engines such as microprocessors, ASIC's, FPGA's etc.:

performing multi-sensor data fusion with the acquired sensor data to determine gait, stance and/or activity parameters if a plurality of sensors is used.

The software can be embodied in a computer program product adapted to carry out the following functions when the software is loaded onto the respective display or displays and executed on one or more processing engines such as microprocessors, ASIC's, FPGA's etc.: validating a single gait, stance and/or activity parameter with the data of multiple sensors if a plurality of sensors is used.

Furthermore the placement of the described components or components with similar purposes is not restricted to the described location on the walking aid. Adaptations, variations or modifications to the invention which are not included in the description above that serve a similar or comparable purpose can be considered to be included within the scope of the present invention.

For the purpose of clarity and a concise description features are described herein as part of the same or separate embodiments, however, it will be appreciated that the scope of the invention may include embodiments having combinations of all or some of the features described". In view of this passage it is evident to the skilled reader that the variants of claim 1 as filed may be combined with other features described in the application as filed, in particular with features disclosed in the dependent claims, such claims usually relating to the most preferred embodiments of an invention.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

The invention claimed is:

1. A method for providing feedback to a user walking with a walking aid, wherein the walking aid comprises at least two cues of a different type, wherein the cue type is any of a visual, auditory or tactile cue type, the method comprising the steps of:

- storing user data, preferences and an acceptable threshold in a user profile,
- recording sensor data with a configuration of at least one sensor positioned on the walking aid while a user is moving,
- determining gait, stance and/or activity parameters from the acquired sensor data,
- comparing the parameters with the user data and preferences to determine if the gait, stance and/or activity parameters fall within the acceptable threshold,
- if the parameters are not within the acceptable threshold, then:
  - verifying using all sensor data and user preferences to validate gait/stance irregularities,
  - verifying the cues status by verifying if one or more cues are already on, and
  - if no cues are on then turn one or more cues on, else based on the user profile and cue status change cue type, intensity or rate of a cue that is on,
- if the parameters are within the acceptable threshold, the gait and/or stance are considered as regular, and then:
  - verifying the cues status by verifying if one or more cues are already on, and
  - if no cues are on then keep the cues off, else determining the next cue action, and wherein based on the user profile and cues status the next cue action is selected from any of: turning the cues off that are on, continuing to maintain the cues on that are on, or lowering the intensity of the cues that are on so as to have them fade away.

2. The method according to claim 1, wherein the step of determining gait, stance and/or activity parameters further comprises the step of performing multi-sensor data fusion with the acquired sensor data to determine gait, stance and/or activity parameters if a plurality of sensors is used.

3. The method according to claim 1, wherein the step of determining gait, stance and/or activity parameters further comprises the step of validating a single gait, stance and/or activity parameter with the data of multiple sensors if a plurality of sensors is used.

4. The method according to claim 1, wherein the cue is generated by a stimulus generating device such as a light source, a display, an electroacoustic transducer, a vibration unit.

5. The method according to claim 1, wherein the configuration of sensors comprises at least one of a camera, a force sensor, a time sensor, a speed sensor, a position sensor, a movement sensor, an inertial sensor, an optical sensor, an ultrasonic sensor, an infrared sensor, a radiographic sensor, and a time of flight sensor.

6. The method according to claim 1, further comprising the step of updating the user profile preferences with the measured data.

7. A non-transitory computer readable medium comprising encoded instructions that, when executed by one or more processors, perform the method of claim 1.

* * * * *